United States Patent [19]

Lahille et al.

[11] Patent Number: 4,957,501
[45] Date of Patent: Sep. 18, 1990

[54] ANTI-EMBOLIC FILTER

[75] Inventors: Michel A. Lahille, Vauhallan; Alain J. Dibie, Paris, both of France

[73] Assignee: Biomat, S.A.R.L., Vauhallan, France

[21] Appl. No.: 290,275

[22] Filed: Dec. 27, 1988

[30] Foreign Application Priority Data

Dec. 31, 1987 [FR] France .................. 87 18472
Jun. 15, 1988 [FR] France .................. 88 08031

[51] Int. Cl.$^5$ ............................... A61M 29/00
[52] U.S. Cl. .................. 606/200; 128/899; 604/104
[58] Field of Search .......... 128/899; 604/104–106; 606/200, 191, 194

[56] References Cited

U.S. PATENT DOCUMENTS

| | | | |
|---|---|---|---|
| 3,540,431 | 11/1970 | Mobin-Uddin | 128/899 |
| 3,952,747 | 4/1976 | Kimmell, Jr. | 606/200 |
| 4,425,908 | 1/1984 | Simon | 128/899 |
| 4,494,531 | 1/1985 | Gianturco | 606/200 |
| 4,619,246 | 10/1986 | Molgaard-Nielsen et al. | 128/899 |
| 4,643,184 | 2/1987 | Mobin-Uddin | 606/200 |
| 4,688,553 | 8/1987 | Metals | 128/899 |
| 4,727,873 | 3/1988 | Mobin-Uddin | 606/200 |
| 4,832,055 | 5/1989 | Palestrant | 128/899 |

OTHER PUBLICATIONS

"New Percutaneous Caval Filter Device for Pulmonary Thromboembolism", by J. Driller et al *Medical and Biological Engineering,* Nov., 1976, pp. 629–635.

*Primary Examiner*—Stephen C. Pellegrino
*Assistant Examiner*—Michael Rafa
*Attorney, Agent, or Firm*—Laubscher, Presta & Laubscher

[57] ABSTRACT

The filter is particularly for implantation in the interior vena cava by sliding through a small sized catheter of type 7F, so as to arrest the migration of all thrombi of dangerous size. The filter comprises a flexible wire having been subjected to a primitive predeformation into first and second substantially flat superposed loops. The loops are substantially symmetrical respectively with regard to two axes which are substantially orthogonal and convergent at a center of the filter. These loops can be elliptic and inscribed in a square, thus providing four contact points with the venous wall, which are in two-to-two symmetry with regard to the center on the longitudinal axis of the vein, which gives the filter high stability in the vein.

21 Claims, 5 Drawing Sheets

ANTI-EMBOLIC FILTER

BACKGROUND OF THE INVENTION

1. Field of the Invention

This invention relates to an anti-embolic filter for the prevention of blood emboli, and more particularly a vena-cava filter against cruor embolism.

The main purpose of the filter is to arrest the migration of thrombi coming from peripheral venous flow of the inferior limbs or lower pelvis and circulating in the direction of the pulmonary arteries, where the thrombi could cause severe and often lethal emboli by obstructing the large branches.

2. Description of the Prior Art

Various inferior-vena-cava filters have been developed and are described in the article by J. DRILLER et al., entitled "New percutaneous caval filter device for pulmonary thromboembolism", in Medical and Biological Engineering, November 1976, New York, pages 629 to 635.

Such a filter generally has an expansible body which is collapsible into a generally cylindrical form so as to introduce it in a catheter and to push it in the latter to the place of implantation of the filter in the inferior-vena-cava. When the body of the filter leaves the catheter, it then spreads out in a revolution form in the vein thereby enlarging the cross-section of the vein and obstructing all dangerous foreign bodies, such as blood clots, liable to cause a pulmonary embolism.

MOBIN-UDDIN holed umbrella disclosed in U.S. Pat. No. 3,540,431 is an endovenous filter which requires surgical access of the internal jugular vein under local anesthesia. The MOBIN-UDDIN filter has several inconveniences. To insert the umbrella filter, it must be folded and screwed into a tubular capsule of an adapter which is pushed by means of a flexible tubular catheter to the place of implantation. The adapter is bulky and does not enable the filter to be introduced through narrow and tortuous jugular veins. Furthermore, the umbrella filter is liable to migrate some distance or to topple. The filter often entails thrombosis, sooner or later, causing an inferior venous stasis syndrome The more recent Lazar J. GREENFIELD filter is comprised of an assembly of stainless steel undulated wires which are connected together by means of a metal capsule and which are unfurled according to conic generating lines, like the struts of an umbrella. The inconveniences of this filter are analogous to those of the MOBIN-UDDIN filter. However, the GREENFIELD filter can be introduced via the femoral vein or the jugular vein, by means of a very high sized introducer of type 24F, having a diameter of 7,92 mm. This filter requires a surgical denudation or a percutaneous access. The plurality of radial filter anchoring hooks due to the sharp and curved free extremities of the wires appears to be traumatic for the venous wall. The malpositions of the filter in the vena cava and the migration of the filter to the heart are not exceptional.

A third endovenous filter, known as the GUNTHER filter, is comprised of a first tubular flexible envelop (basket) comprised of predeformed axially twisted metal wires, and of a set of curved wires attached at one extremity of the envelop and analogous to a GREENFIELD filter. When the filter is unfurled, the envelop has a longitudinal section substantially delimited by two opposite sinusoidal alternations. The radially compressed envelop of the GUNTHER filter has still a relatively large diameter requiring the use of a large introducer catheter of the 10F type, corresponding to a diameter in the order of 3.3 mm.

All these known filters also necessitate complex equipment that is specially designed to introduce the filter into a particular catheter of great size 9F to 24F. Indeed, the filter must be pulled into a sheath, also called as an adapter or cartridge, by means of a hook so as to reduce its cross-section to the internal cross-section of the catheter, then the sheath is plugged into a proximal extremity of the catheter, so as to push the filter in the catheter. With all known filters, their reduced cross section in the catheter depends on the great number of wires bunched together, which restricts the use of these filters to veins of relatively large diameter, or at least, increases the duration and the difficulties of the surgical operation.

OBJECTS OF THE INVENTION

The main object of this invention is to remedy the main preceding disadvantages of the aforesaid anti-embolic filters.

Another object of this invention is to provide an anti-embolic filter which has a very small cross-section for its introduction without risk of catching in a small sized catheter for use of veins in superior limbs.

A further object of this invention is to use a simple and inexpensive equipment to introduce an anti-embolic filter into a standard catheter.

Still another object of this invention is to provide an anti-embolic filter which, when implanted, is balanced and stable in the vein by its very nature and is not in danger of migrating.

SUMMARY OF THE INVENTION

Accordingly, an anti-embolic filter embodying the invention, to be implanted in a physiological canal, comprises a flexible wire having been subjected to a primitive predeformation into first and second substantially flat superposed loops. The loops are substantially symmetrical respectively with regard to two axes which are substantially orthogonal and convergent at a centre of the filter.

The wire can be spread out in an almost rectilinear condition so as to be easily introduced into a catheter of small external diameter, typically equal to 2.3 mm, by simple successive manual pushes. Any venous access can be selected, such as jugular vein, femoral vein, cephalic vein or humeral vein. The small diameter of the catheter and its suppleness which is not impaired by the threading of the filiform filter into the catheter, enables various vein meanderings to be travelled without aggressing the venous wall. E.g., the catheter threading the humeral vein of a superior limb can travel the right atrium to position the proximal extremity of the catheter in exactly the place desired, in the inferior-vena-cava.

Because of the wire elasticity, the wire recalls its primitive configuration of two preferably elliptic or oblong crossed loops as soon as the wire leaves the catheter in the physiological canal, such as the vena cava. The loops are generated according to the longitudinal direction of the vein. The flatness of the filter thus expansed and having a diameter more than that of the vein imposes a transversal flat section of the vein, substantially close to an ellipse having an eccentricity near one, which is intersected by the various traversals of the arcs of the two superposed loops which arrest all possible migration of blood clots considered to be of dangerous size.

The loops are unfurled according to the direction of the blood flow longitudinal to the vein. However, the filter is stable as a result of its quasi-symmetry. Indeed, the loops can be inscribed in a square. Each of the loops is tangential to two parallel sides of the square, i.e., in practice, the loops lean against the venous wall at four contact points in two to two symmetry with regard to the centre of the filter. These contact points do not harm the venous wall and will be intimately bound to it by endothelialisation a few days after implantation of the filter.

As well as this symmetry of the filter must be added the fact that the wire is initially predeformed into two loops, from a first free extremity of the first loop towards a second free extremity of the second loop, according to a same rotation direction around the centre of the filter, and without going against the wire drawing of the wire. Subsequently, the compression exerted on the filter by the venous wall does not tend to spread out the filter so that it migrates in the vein, as is the case with certain filters embodying the prior art.

According to other features of the invention, the extremities of the filter each comprise a small cylindrical or truncated revolution weight which leans against the venous wall. The weights are situated near the centre of the filter and laterally to it. Moreover, the second filter extremity, called as distal extremity, introduced last in the catheter and the vein, offers preferably a substantially rectilinear direction inclined at an angle of approximately 45° with regard to the plan of the loops. The second extremity comprises, at the rear of the weight, a sharp tip which substantially enters the venous wall slantwise though without traversing it, due to the stop role of the weight. The sharp tip increases the stability of the filter.

The invention also relates to a pusher member particularly intended to receive the second extremity of the filter so as to push the filter in the catheter and to eject it in the vein, but also, if necessary, to pull it towards the rear in the catheter so as to check and adjust the position of the filter. The pusher member comprises from an extremity, a first longitudinal groove for receiving a short length of the filter wire behind the revolution weight, and a longitudinal notch for receiving the second weight whereby the weight be completely embedded in the pusher. The pusher preferably comprises a second groove colinear with the first groove and emerging into the notch for receiving the tip prolonging the revolution weight. Subsequently, the first extremity of the filter which only comprises one weight, guides the wire by gentle sliding in the catheter, and the sharp tip at the second extremity does not hinder the advance of the pusher in the catheter as the second extremity is entirely embedded in the pusher.

BRIEF DESCRIPTION OF THE DRAWING

The foregoing and other objects, features and advantages of the invention will be apparent from the following detailed description of several embodiments of the invention with reference to the corresponding accompanying drawings in which.

DESCRIPTION OF THE PREFERRED EMBODIMENTS

Figure 1:
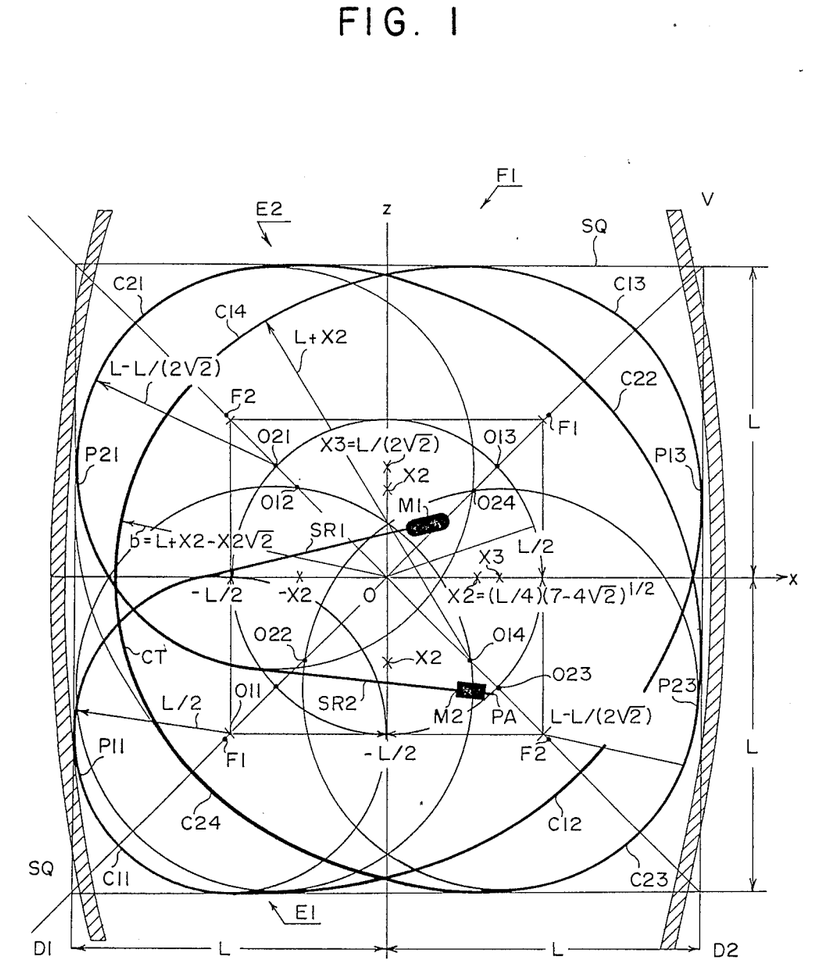
FIG. 1 is a flat longitudinal view of a two orthogonal elliptic loop anti-embolic filter embodying the invention, placed in a longitudinal section of a vein.
Figure 2:
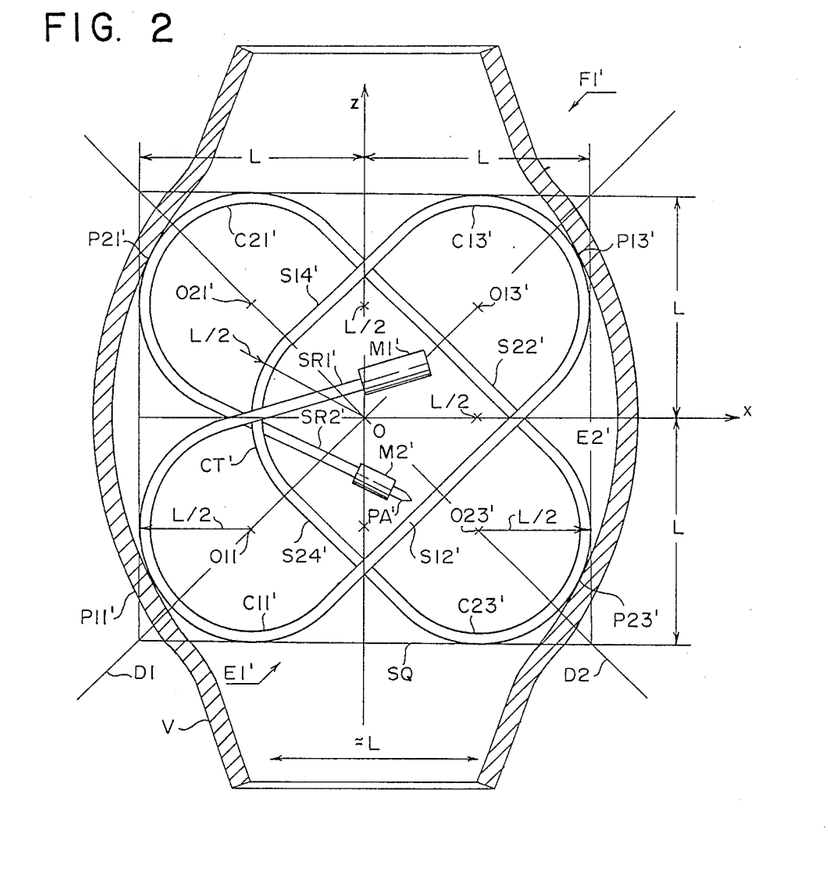
FIG. 2 is a flat longitudinal view of a two orthogonal oblong loop anti-embolic filter embodying the invention, placed in a longitudinal section of a vein.

According to the two preferred embodiments illustrated in FIGS. 1 and 2, an anti-embolic filter embodying the invention is realized from a flexible and elastic radio-opaque wire, preferably in cobalt-chrome alloy, which has been subjected to a primitive predeformation. The predeformation memorizing properties of the wire enable the wire to be unfurled, e.g. in a rectilinear condition by stretching both extremities thereof, and, after releasing the wire extremities, to recall the predeformation configuration due to the spring effect of the wire.

According to the first preferred embodiment shown in FIG. 1, the primitive predeformation gives the wire a configuration with two flat oval loops, very much like two substantially identical ellipses E1 and E2 with orthogonal major axes D1 and D2. The filter FI thus formed is inscribed in a square SQ of side 2L whose diagonals are coincidental with the major axes D1 and D2, and the centre O is coincidental with those of the two elliptic loops E1 and E2. In FIG. 1, the first loop E1 is superposed on the second loop E2.

In order to set the ideas straight, the geometry of the filter FI is indicated in detail hereafter in reference to a Cartesian reference system centered at O and having an abscissa-axis Ox and a side-axis Oz that are respectively horizontal and vertical and that bisect the diagonals D1 and D2 of the square SQ.

The first loop E1 can be broken up from a first free extremity M1 of the filter FI located in the region of the centre O in the first quadrant of the reference system Ox, Oz, into:

a rectilinear or substantially convex segment SR1 tangential to a circle C11 with a centre O11 of co-ordinates $-L/2$, $-L/2$ and a radius equal to $L/2$, an arc of the circle C11 having a length substantially inferior to the semi-circumference of the circle C11 and ending substantially at the tangent point of the circle C11, on the lower side of the square SQ, a circle arc C12 substantially traversing in diagonal the fourth quadrant of the reference system Ox, Oz, with a centre O12 of co-ordinates $-X2 = -(L/4)(7-\sqrt{2})^{\frac{1}{2}}$, X2, and a radius equal to $L+X2$, the arc C12 having extremities tangential to the circle arc C11 and a circle arc C13 opposite to the arc C11 with regard to the centre O, the circle arc C13 with a centre O13 of co-ordinates $X3=L/(2\sqrt{2})$, X3, and a radius equal to $L-X3$, and extending tangentially between the two adjacent sides of the square SQ in the first quadrant of the reference system, and a fourth circle arc C14 coming from a circle symmetrical to that of the circle arc C12 with regard to the centre O, with a centre O14 of co-ordinates X2, $-X2$ and a radius equal to $L+X2$, and extending tangentially from the circle arc C13 to the second diagonal D2.

Between the elliptic loops E1 and E2, the filter FI presents a transition comprised of a quarter CT of a circle having point O as centre, and a radius equal to $b=L+X2(1-\sqrt{2})$, and secant of the axis Ox and extending tangentially between the arc C14 and a first circle arc C24 of the second loop E2.

The second loop E2 is deducted from the first loop E1 according to a symmetry of the arcs C14, C13, and C12 with regard to the axis Ox. The second loop E2 can thus be broken up from the extremity of the transition arc CT on the diagonal D1 located in the third quadrant of the reference system Ox, Oz, into a circle arc C24 identical to the arc C14, with a centre O24 of co-ordinates X2, X2 and a radius equal to $L+X2$, and extending to the lower side of the square SQ, a circle arc C23 identical to the arc C13, with a centre O23 of co-ordinates $X3=L/(2\sqrt{2})$, $-X3$ and a radius equal to $L-X3$, and extending tangentially between the two adjacent sides of the square SQ in the fourth quadrant, a circle arc C22 substantially identical to the arc C12, substantially traversing in diagonal the first quadrant, and having a centre O22 of co-ordinates $-X2$, $-X2$ and a radius equal to $L+X2$, a circle arc C21 coming from a circle symmetrical to that of the arc C23 with regard to the centre O, with a centre O21 of co-ordinates $-X3$, X3 and a radius equal to $L-X3$, and substantially extending on a semi-circumference to the third quadrant, and passing under the transition arc CT and the circle arc C11, and a rectilinear or substantially convex segment SR2 tangential to the circle arc C21, at a point having an abscissa substantially equal to $-L/2$, and extending to a second free extremity M2 of the filter FI located in the fourth quadrant, near the centre O and substantially symmetrical to the first free extremity M1 with regard to the axis Ox.

It thus appears that the filter FI comprises two convex closed curves which are substantially generated according to two ellipses E1 and E2 having orthogonal major axes of length $2a=3L-L/\sqrt{2}$ and orthogonal minor axes of length $2b=2(L+X2(1-\sqrt{2})$ equal to the diameter of the transitional arc CT. Focal points F1 and F2 of the two loops E1 and E2 are respectively situated on the diagonals D1 and D2 and at a distance from the centre O equal to $c=(a^2-b^2)^{\frac{1}{2}}$.

According to another variant of the first embodiment, the first circle arc C11 of the first loop E1 can have a greater radius, e.g. equal to the radius L-X3 of the circle arcs C13, C23 and C21.

Figure 3:
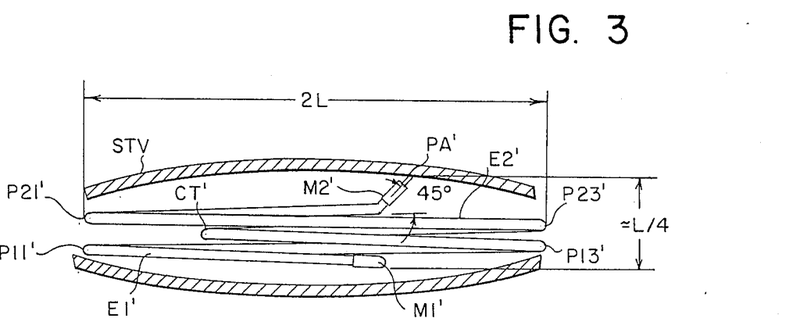
FIG. 3 is a transversal view of the filter and the vein in FIG. 2.

Referring to FIGS. 2 and 3, a filter FI' embodying a second realization comprises a wire having been subjected to a primitive predeformation giving two superposed oblong flat loops E1' and E2'. Loops E1' and E2' have orthogonal major axes D1 and D2 and are also inscribed in a square SQ of side 2L and centre O. Each of the loops E1' and E2' is substantially comprised of two semi-circles C11' and C13', C21' and C23' having centres O11' and O13', O21' and O23' equidistant from $L/\sqrt{2}$ with regard to the centre O and situated on the respective diagonal D1, D2, and having radiuses equal to $L/2$. Like the circle arcs C11, C23, C13 and C21 in FIG. 1, the semi-circles C11', C23', C13' and C21' are situated in the four corners of square SQ and are each tangential to two respective adjacent sides of the square. Most of the extremities of the semi-circles are connected by straight line segments, or substantially convex segments, which are parallel to the respective diagonals D1, D2 and are of length $L\sqrt{2}$. Each of the loops E1' and E2' thus has a major axis with length $L(1+\sqrt{2})$ and a minor axis with length L.

The first loop E1' is comprised of a rectilinear or substantially convex segment SR1' between a first free extremity M1' of filter FI' substantially located on the diagonal D1 in the region of the centre O, in the first quadrant, and an extremity of the semi-circle C11' substantially on the axis Ox, of the semi-circle C11', of a straight line segment S12' of length $L\sqrt{2}$ connecting the extremities of the semi-circles C11' and C13' and parallel to the diagonal D1, of the semi-circle C13', and of a straight line segment S14' of length $L/\sqrt{2}$ parallel to the diagonal D1 and prolonging the semi-circle C13' into the second quadrant to the diagonal D2.

Likewise, the second oblong loop E2' comprises a straight line segment S24' of length $L/\sqrt{2}$ which is parallel to the diagonal D2 and symmetrical to the segment S14' with regard to the axis Ox. A quarter of a transition circle CT' of radius $L/2$ and centre O connects the near extremities of the segments S14' and S24'.

The second loop E2' is thus comprised of the segment S24' of length $L/\sqrt{2}$, of the semi-circle C23', of a straight line segment S22' which is parallel to the diagonal D2, is of length L and joins extremities of the semi-circles C23' and C21' respectively near the axes Ox and Oy, of the semi-circle C21', and of a straight line segment or substantially convex segment SR2' prolonging the semi-circle C21' in the direction of the fourth quadrant, passing below the semi-circle C11' and the quarter of a circle CT', and ended by a second free extremity M2' of the filter FI'.

It should be noted that the first filter FI is more easily coiled into its two-loop configuration than the second filter FI', due to a replacement of rectilinear segments S12', S14', S24' and S22' by the big circle arcs C12, C14, C24 and C22. According to other embodiments, every convex loop arc can be approximated by a convex polygonal line.

When placed in a physiological canal, such as a blood vessel or a vein V, having a cross sectional diameter substantially lower than L, the bisecting axis Oz of the diagonals of the square SQ colinear with the major axes of the loops E1 and E2, E1' and E2' coincides with the longitudinal axis of the vein V. In a longitudinal section of the vein V, as shown in FIGS. 1 and 2, the vein V is enlarged substantially to a width 2L over a short length substantially equal to 2L not exceeding 40 mm approximately. This reduces all the more the risk of malposition of the filter in a collateral vein. The length 2L is selected in such a way that it is inferior to the space between two vertebrae. In practice, the length 2L can be between 25 and 36 mm. The vein V leans against the filter at four contact points P11, P23, P13 and P21, P11', P23', P13' and P21' in two to two symmetry with regard to the axes Ox and Oz, and tangentially to the four circle arcs C11, C23, C13 and C21, C11', C23', C13' and C21' situated in the four corners of the square SQ. The filter thus positioned is in permanent tension equilibrium, while being relatively short in the longitudinal direction of the vein V, which avoids any migration of the filter in either longitudinal direction.

Seen in transversal section, as shown in FIG. 3, the four contact points are also substantially symmetrical with regard to orthogonal transversal axes Ox and Oy of the vein V. The filter is very flat and decreases the cross section of the vein from a circular section with a diameter in the order of L to an elliptic section STV of major axis 2L and minor axis L/4 approximately, and thus having an eccentricity very close to one. The filter wire traverses six times the minor axis Oy of the transversal section of the vein. These transversals as well as the flat longitudinal nature of the filter contribute to the arresting of all foreign bodies of a size considered dangerous carried by the venous flow, such as a blood clot or embolus, without interrupting the blood flow rate, the filter itself not being thrombogenic.

The filter embodying the invention also has another interesting property. The filter wire constantly follows a single rotation direction around the centre O, from the first extremity M1 towards the second extremity M2, in a longitudinal plane of the vein V, e.g. in counterclockwise direction according to the embodiments shown in FIGS. 1 and 2. This property gives the filter, on one hand, a perfect equilibrium despite the compression exerted by the venous wall, around the centre O, which avoids all unfurling of the filter in the longitudinal direction of the vein as a result of the centrifugal elasticity of the wire, and, on the other hand, an instantaneous recall of its initial configuration when the filter is ejected in the vein. As will be apparent hereinafter, as long as the filter has not been totally ejected from the proximal extremity of a catheter, the filter can be unfurled to partially form the first loop, then the second loop, or be partially or entirely retracted from the vein so as to position it properly.

E.g., the filter wire is of 0.3 mm diameter, and its length varies between 160 and 260 mm approximately, according to the length 2L selected. The initial predeformation of the wire is obtained according to a known process which consists of a predeformation in the cold state of the wire according to the configuration selected by means of calibrating cylinders with radiuses substantially equal to those of the different circle arcs of the loops, then of a quench hardening after the wire has been brought to a temperature of 500° C. for approximately three hours. This quench hardening increases the hardness of the wire.

Figure 4:
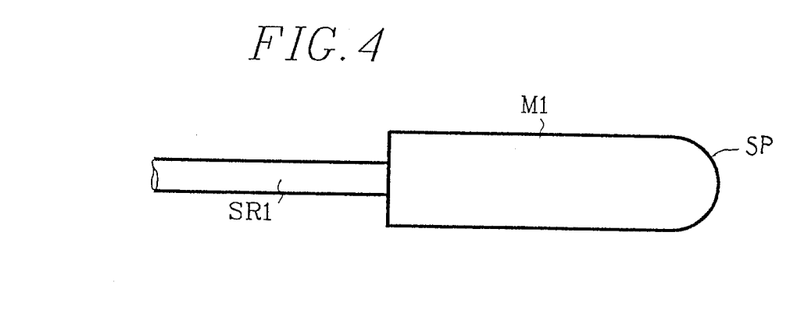
FIG. 4 is a detailed longitudinal view of a first extremity of a first loop of a filter embodying the invention.

As shown in FIG. 4, the first extremity, called as proximal extremity, of the filter FI, FI' which is first to come into contact with the vein V during the ejection operation, is designed as a small revolution weight M1, M1', in this case cylindrical and coaxial with the wire, with a typical length of 4 mm. The diameter of the weight M1', M1 lies between 0.6 and 1 mm, thereby enabling the weight to slide freely in the vein V and in a standardized catheter, e.g. of size 7F of internal diameter 1.45 mm. Unlike the wire, the extremity of the weight M1, M1' comprises a hemispherical rounding SP so as to facilitate the entry of the filter in the vein V without agressing the vein and consequently the venous endothelium, while providing the latter with a relatively large contact surface.

Figure 5:
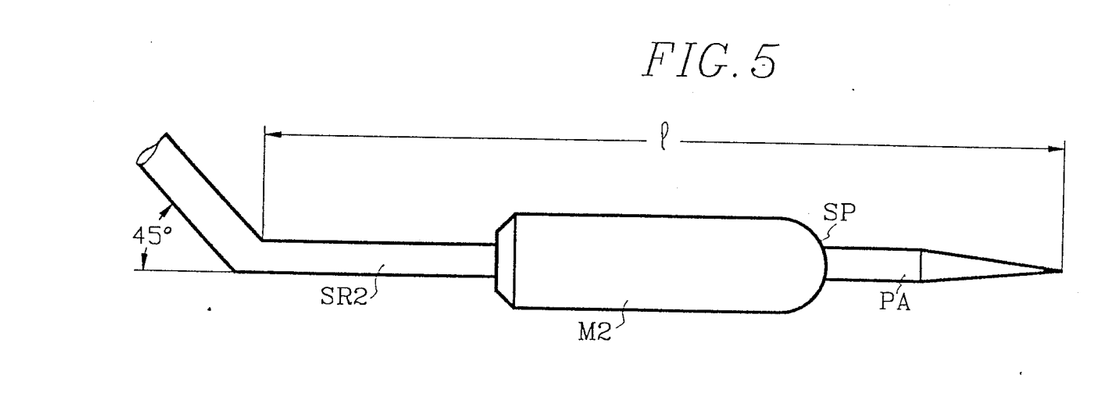
FIG. 5 is a detailed longitudinal view of a second extremity of a second loop of a filter embodying the invention.

As shown in FIG. 5, the second extremity of the filter FI, FI', which is last to enter the catheter and the vein, also comprises a revolution weight M2, M2', in this case cylindrical and coaxial with the wire and having a length equal to that of the weight M1, M1' but a smaller diameter, typically of 0.6 mm. However, the second weight M2, M2' is prolonged by a sharp axial tip PA, conic or bevelled, with a typical diameter of 0.3 mm and length of 3 mm. This tip PA is intended to embed itself lightly into the wall of the vein V after ejection of the filter, thereby anchoring the filter according to its primitive configuration in the selected place of the vein. Furthermore, this tip PA with the weight M2, M2' increases the embedding surface of the second extremity of the filter in a catheter pusher, as will be apparent hereinafter.

As shown in FIGS. 3 and 5, the second extremity of the filter in transversal view is preferrably inclined at an angle of approximately 45° with regard to the distal segment SR2, SR2' and, more generally, at an angle of approximately 45° with regard to the longitudinal plan Ox, Oz of loops E1 and E2, E1' and E2', over a length l of about ten millimeters, so as to enter the venous wall slantwise and therefore over a greater length than if the tip PA were to enter perpendicularly to the venous wall. The rounding SP of the second weight M2, M2' abuts against the venous wall and restricts the entry of the tip PA.

The weights are attached in coaxial relation to the filter wire extremities, e.g. by microsoldering, and the tip PA can be a shaped extremity of the wire. Instead of being cylindrical, the weights can be susbtantially truncated in the shape of a conic frustrum or an ellipsoid.

To implant the filter, such as the filter FI, the invention requires a traditional catheter 3, of typical size 7F, i.e., with internal and external diameters of 1.45 mm and 2.3 mm, and a length of approximately 1 m. Catheter 3 is a long copolymer tube with a thin inner wall having a low coefficient of friction for easy sliding of a filter pusher 4 embodying the invention. The catheter comprises a cylindrical socket at its distal extremity through which the filter is introduced and then the pusher slid.

Figure 6:
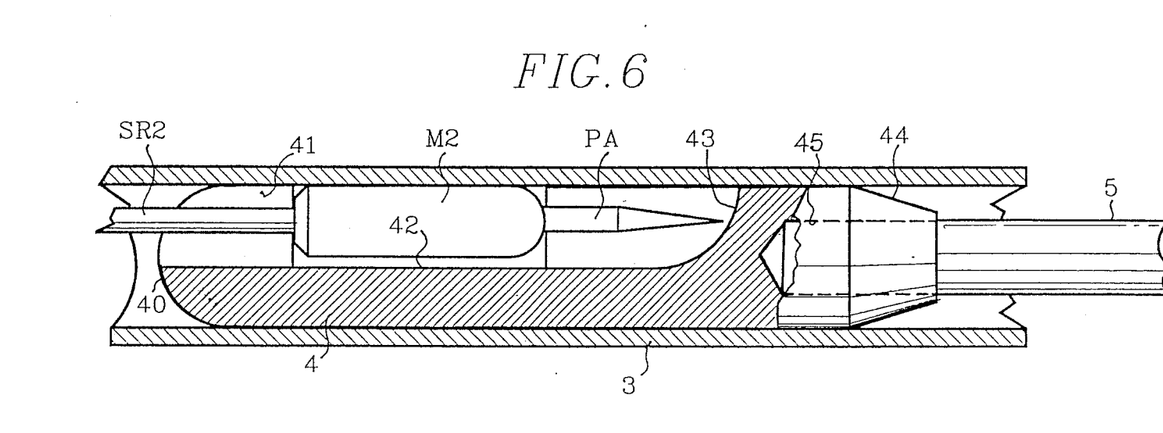
FIGS. 6 and 7 are respectively longitudinal side and top views of a pusher embodying the invention, comprising a second filter extremity and included in a catheter.
Figure 7:
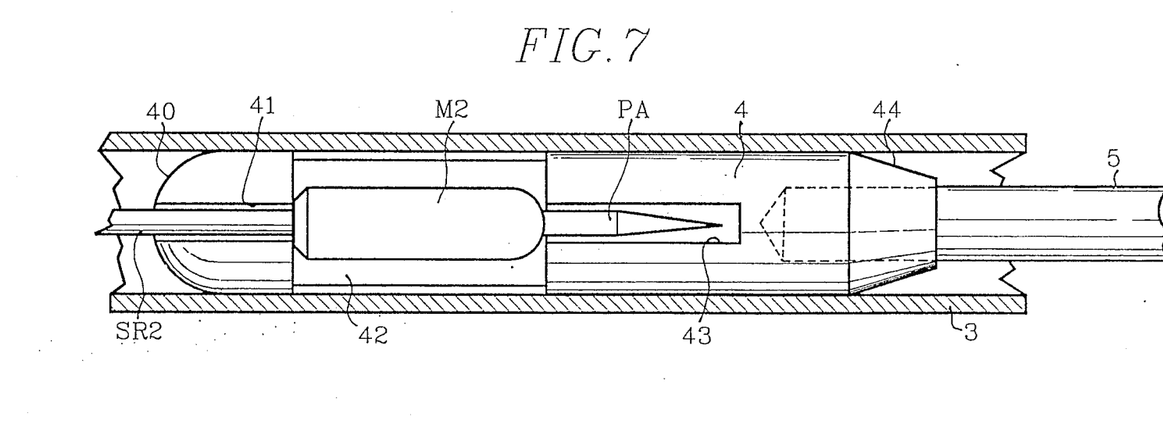

As shown in detail in FIGS. 6 and 7, the pusher 4 embodying the invention intended to receive the second extremity M2+PA of the filter FI is made up of a solid cylindrical socket having an external diameter substantially less than the internal diameter of the catheter and typically equal to 1.3 mm, and having a length substantially equal to twice the length of the weight M2 and sharp tip PA assembly.

From a first hemispherical extremity 40 of the pusher which enters the catheter 3 first, the pusher 4 comprises a small longitudinal groove 41, a laterally open longitudinal notch 42, and a second longitudinal groove 43 which is a pocket groove. The grooves 41 and 43 are colinear according to a longitudinal and axial plane of the pusher 4, have a depth more than the diameter of the weight M1, and typically equal to the sum of the radiuses of the pusher and the filter wire FI, and a width substantially more than the diameter of the filter wire. The bottom of the notch 42 is flat and perpendicular to the walls of the grooves 41 and 43. The depth of the notch 42 can be equal to or more than that of the grooves. The length of the notch 42 and the length of the rectilinear bottom of the groove 43 are respectively substantially more than those of the weight M2 and the tip PA. The length of the first groove 41 is in the region of 2 mm.

At a second truncated extremity 44 of the pusher 4 is provided an axial pocket hole 45 to receive by snug fitting and glueing an extremity of a stainless steel braided wire 5 with a typical diameter of 0.8 mm and considerably longer than the catheter 3.

The implantation proper of the filter FI follows the introduction of the catheter 3, in a traditional manner, by percutaneous path and local anesthesia, e.g. via the femoral, humeral, cephalic or jugular vein, by means of an introductory guidewire having a proximal extremity equipped with a Teflon cylindrical guide which is pushed along the vein to the selected place of implantation. The catheter slides along the guidewire, then the guidewire is withdrawn from the interior of the catheter. The proximal extremity of the catheter is thus located ahead of the selected place of implantation, by X-ray examination, as is the entire implantation of the filter FI described hereinafter.

The first weight extremity M1 of the filter FI is introduced in the external distal cylindrical socket of the tubular catheter 3. Then the extremity M1 slides in the catheter through the exerting of numerous manual pushes on the filter wire which is progressively brought to a substantially rectilinear condition and which follows the tortuous path of the catheter. This traveling of the filter FI in the catheter continues until the second extremity M2+PA of the filter is ahead of the distal socket of the catheter.

At this stage, unless it has already been done, the second weight M2 is lodged in the notch 42 of the pusher 4, and simultaneously the tip PA and the extremity of the wire segment SR2 of the filter FI are respectively lodged into the grooves 43 and 41, in such a manner that the extremity M2+PA does not jut out radially over the pusher 4. The distal extremity M2+PA thus held in the pusher 4 and momentarily firmly housed in the latter is introduced into the catheter 3 by means of a rectilinear conical introducer sleeve. The pusher with the distal extremity of the filter slides from the introducer sleeve into the distal extremity of the catheter.

Figure 8:
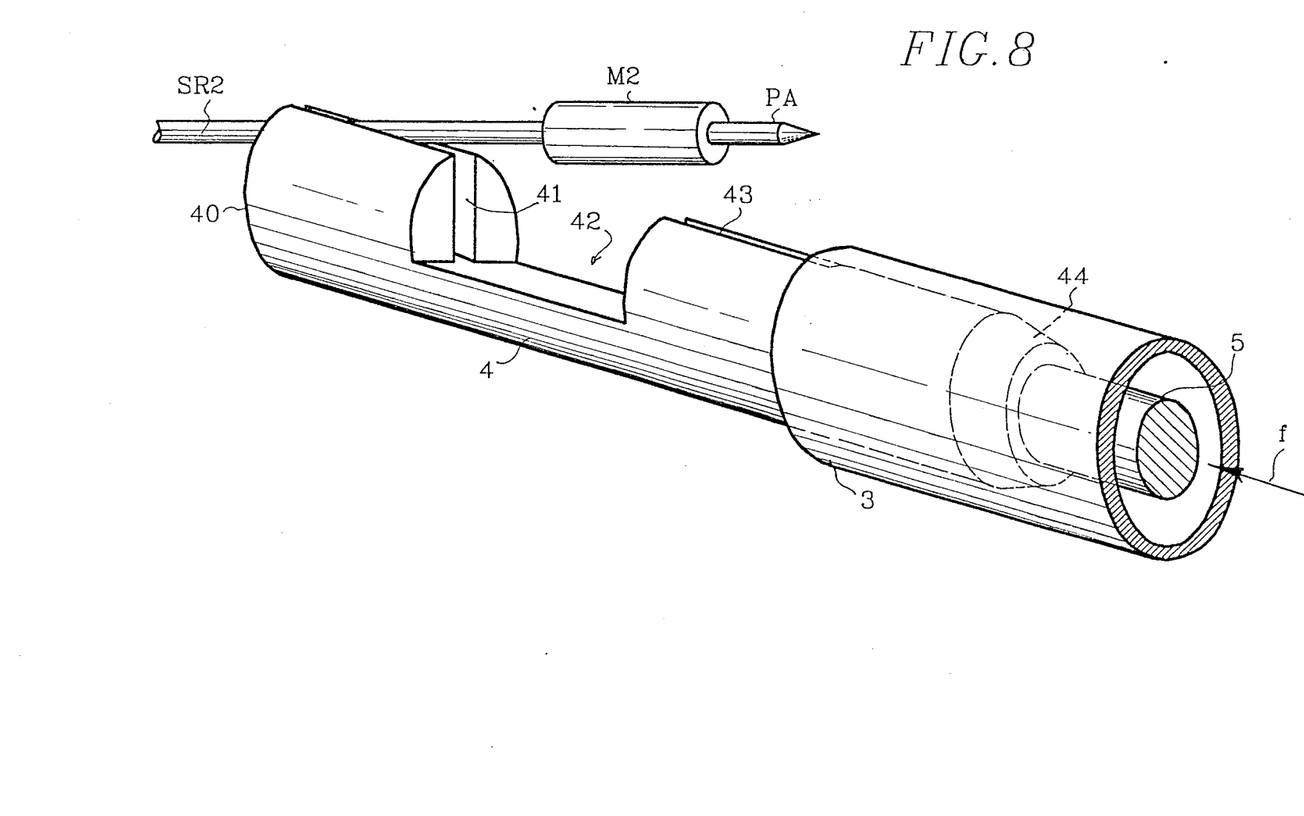
FIG. 8 is a schematic view in perspective of the pusher partially leaving a proximal extremity of the catheter at the time of ejection of a filter embodying the invention into a vein.

The filter FI then continues to slide in the catheter 3 towards the proximal extremity of the catheter in the vein, and the pusher 4 slides in the catheter, in the direction of the arrow f in FIG. 8, due to successive manual pushes exerted on the pusher wire 4 which in turn enters the catheter When the proximal extremity M1 of the filter emerges from the catheter 3 in the vein V, the filter wire progressively recalls its primitive configuration of two orthogonal loops E1 and E2 in the vein V.

The location of the filter can be adjusted, e.g. by only freeing the length of the filter corresponding to the first loop E1, and by pulling and pushing over a short length the pusher wire 5 which is, at this stage, completely firmly attached to the filter FI due to the embedding of the extremity M2+PA in the pusher 4. If need be, the filter can be recuperated by completely withdrawing the wire 5 and the pusher 4 from the catheter 3, or, if necessary, the catheter 3 is pulled or pushed lightly to position the proximal extremity of the catheter with precision ahead of the selected place of implantation of the filter, e.g. between two determined vertebrae, along the inferior vena cava.

Finally, the filter FI is ejected, as shown in FIG. 8, as soon as the notch 42 and grooves 41, 43 extremity of the pusher 4 leaves the proximal extremity of the catheter 3, and more precisely, as soon as the pocket groove 43 enters the vein. However, the other extremity 44 of the pusher, behind the groove 43, remains in the catheter so as to facilitate the withdrawal of the pusher 4 from the catheter 3, by pulling the pusher wire 5 in the opposite direction to the arrow f. Due to the elasticity of the filter wire, the filter FI deforms itself to progressively recall its initial two-loop configuration during its entry in the vein, and the extremity M2+PA is automatically disengaged from the pusher to stop against the venous wall, as shown in FIG. 3. The tip PA located in a plan perpendicular to the plan of the filter loops substantially enters the venous wall at an angle of 45° without traversing it nevertheless, due to the rounded extremity SP of the second weight M2 which abuts against the venous wall. The filter FI is thus definitively implanted in the vein V.

An endothelialisation occurs after a few days. The peripheral portions of the loops E1, E2, at the contact points P11, P23, P13 and P21, as well as the distal extremity M2+PA of the filter become integrated into the venous wall, giving the filter a definitive stability and preventing all risks of migration of the filter in the vein, notably towards the heart and the pulmonary arteries.

According to another embodiment, the external distal extremity of the catheter 3 can comprise a Y-branching of which a first branch is collinear with the rest of the catheter to introduce the filter FI and the pusher 4, and of which the other lateral branch is inclined with regard to the first branch so as to inject a lubrifying liquid product, preferably radio-opaque, which improves the sliding of the pusher 4 in the catheter 3, and contributes to the locating of the position of the proximal extremity of the catheter in the vein V.

What we claim is:

1. An anti-embolic filter for implantation in a physiological canal, said filter comprising a single flexible wire, and means connected with said wire for anchoring said filter in a physiological canal, said wire having been subjected to a primitive predeformation into first and second substantially flat superposed loops, said loops being substantially symmetrical respectively with regard to two axes which are substantially orthogonal and convergent at a centre of said filter.

2. The filter claimed in claim 1, wherein said loops are inscribed in a square having said axes as diagonals and having sides of predetermined length 2L where 12.5 mm$<$L$<$18 mm.

3. The filter claimed in claim 2, wherein the filter has a thickness substantially equal to or less than L/4.

4. The filter claimed in claim 2, wherein each of said loops is tangential to two parallel sides of said square at two contact points substantially symmetrical with regard to said centre.

5. The filter as claimed in claim 2, wherein in a transversal view of said loops, said filter is substantially circumscribed by a transversal ellipse of major axis 2L and minor axis L/4 approximately.

6. The filter claimed in claim 5, wherein it comprises four loop contact points with said transversal ellipse.

7. The filter claimed in claim 1, wherein said first and second loops are convex and generated from a first free extremity towards a second free extremity of said filter according to a same rotation direction around said centre.

8. The filter claimed in claim 1, wherein said loops are elliptic.

9. The filter claimed in claim 8, wherein each of said elliptic loops has a major axis substantially equal to $3L-L/\sqrt{2}$ and a minor axis substantially equal to $-2(L+X2(1-\sqrt{2}))$, whereby 2L denotes the length of sides of a square in which said loops are inscribed, where 12.5 mm.$<L<18$ mm. and $X_2$ is equal to $(L/4)(7-4\sqrt{2})^{\frac{1}{2}}$.

10. The filter claimed in claim 9, wherein said loops are connected therebetween substantially by a quarter of a circle of said wire concentric at said centre.

11. The filter claimed in claim 1, wherein said loops are oblong.

12. The filter claimed in claim 11, wherein each of said oblong loops has a major axis substantially equal to $L(1+\sqrt{2})$ and a minor axis substantially equal to L, whereby 2L is the length of sides of a square in which said loops are inscribed and 12.5 mm$<L<18$ mm.

13. The filter claimed in claim 12, wherein said loops are connected therebetween substantially by a quarter of a circle of said wire concentric at said centre.

14. The filter claimed in claim 1, wherein free extremities of said filter comprised of a first extremity of said first loop and a second free extremity of said second loop are located inside said loops, in the region of said centre.

15. The filter claimed in claim 1, wherein said means for anchoring said filter comprise first and second small revolution weights attached to the free extremities of said first and second loops, respectively.

16. The filter claimed in claim 15, wherein said weights have diameters less than 1.45 mm.

17. The filter claimed in claim 15, wherein said second weight is prolonged by a tip which substantially enters the side wall of said physiological canal without traversing, it.

18. The filter as claimed in claim 15, wherein the axis of said second weight is inclined by approximately 45° with regard to the plan of said loops.

19. A cylindrical pusher member intended to slide in a catheter and to receive a small revolution weight on a free extremity of a predetermined flexible wire constituting an anti-embolic filter, said pusher comprising from an extremity, a first longitudinal groove for receiving a short length of said filter wire behind said revolution weight, and a longitudinal notch connected with said groove for receiving said revolution weight whereby said weight be completely embedded in said pusher.

20. A pusher as claimed in claim 19, having a diameter substantially equal to 1.3 mm thereby introducing it into a catheter having internal and external diameters of approximately 1.45 mm and 2.3 mm.

21. A cylindrical pusher member intended to slide in a catheter and to receive a free extremity of a predeformed flexible wire constituting an anti-embolic filter, said wire extremity comprising a small revolution weight prolonged by a tip, and said pusher comprising from an extremity, a first longitudinal groove for receiving a short length of said filter wire behind said revolution weight, a longitudinal notch connected with said first longitudinal groove for receiving said revolution weight whereby said weight be completely embedded in said pusher, and a second groove colinear with said first groove and emerging into said notch for receiving said tip prolonging said revolution weight.

* * * * *